(12) United States Patent
Gmeiner (10) Patent No.: US 12,319,915 B2
(45) Date of Patent: Jun. 3, 2025

(54) CYTOTOXIC FLUOROPYRIMIDINE POLYMERS AND METHODS OF USE THEREOF

(71) Applicant: Wake Forest University Health Sciences, Winston-Salem, NC (US)

(72) Inventor: William H. Gmeiner, Yadkinville, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 1226 days.

(21) Appl. No.: 17/058,989

(22) PCT Filed: May 24, 2019

(86) PCT No.: PCT/US2019/033902
§ 371 (c)(1),
(2) Date: Nov. 25, 2020

(87) PCT Pub. No.: WO2019/226980
PCT Pub. Date: Nov. 28, 2019

(65) Prior Publication Data
US 2021/0214730 A1    Jul. 15, 2021

Related U.S. Application Data

(60) Provisional application No. 62/676,511, filed on May 25, 2018.

(51) Int. Cl.
*C12N 15/113* (2010.01)
*A61K 9/00* (2006.01)
(Continued)

(52) U.S. Cl.
CPC ........ *C12N 15/1137* (2013.01); *A61K 9/0019* (2013.01); *A61K 45/06* (2013.01); *A61P 35/04* (2018.01); *C07H 21/04* (2013.01)

(58) Field of Classification Search
CPC .. C12N 15/1137; A61K 9/0019; A61K 45/06; A61P 35/04; A61P 35/00; C07H 21/04
See application file for complete search history.

(56) References Cited

U.S. PATENT DOCUMENTS

| | | | |
|---|---|---|---|
| 6,342,485 B1 | 1/2002 | Gmeiner | |
| 8,940,885 B2 * | 1/2015 | Gmeiner | ................ C40B 20/06 536/24.5 |

(Continued)

FOREIGN PATENT DOCUMENTS

WO    WO-2009014887 A2 *    1/2009    ......... A61K 31/7105

OTHER PUBLICATIONS

Huang et al. 1991. Action of 2',2'-Difluorodeoxycytidine on DNA Synthesis. Canc. Res. 51:6110-6117 (Year: 1991).*

(Continued)

*Primary Examiner* — Kimberly Chong
*Assistant Examiner* — Ruth Sophia Arieti
(74) *Attorney, Agent, or Firm* — FOX ROTHSCHILD LLP (57) ABSTRACT

Novel cytotoxic fluoropyrimidine polymers for treating cancer (e.g., colorectal cancer (CRC)) in a subject (e.g., a subject having cancer) are nucleic acid molecules including 5-fluoro-2'deoxyuridine monophosphate (FdUMP)[10] having a polyethylene glycol (PEG) spacer appended to the 5' terminus and a cytarabine (AraC) nucleotide appended to 3'termius. These novel cytotoxic fluoropyrimidine polymers may be used in compositions, kits and methods for treating advanced and high-risk cancers, including CRC.

22 Claims, 7 Drawing Sheets
Specification includes a Sequence Listing.

(51) Int. Cl.
  *A61K 45/06*    (2006.01)
  *A61P 35/04*    (2006.01)
  *C07H 21/04*    (2006.01)

(56) References Cited

U.S. PATENT DOCUMENTS

| | | | |
|---|---|---|---|
| 9,012,422 B2* | 4/2015 | Gmeiner | A61P 35/02 |
| | | | 536/25.5 |
| 9,096,853 B2* | 8/2015 | Schmitz, Sr. | C12N 15/111 |
| 9,284,559 B2* | 3/2016 | Gmeiner | A61K 31/713 |
| 2017/0151240 A1 | 6/2017 | Gmeiner | |

OTHER PUBLICATIONS

Perrino et al. 1994. Identification of a 3'-->5'-Exonuclease That Removes Cytosine Arabinoside Monophosphate from 3' Termini of DNA. JBC 269[23]:16357-16363 (Year: 1994).*

Liu ( et al. 2002. Efficacy and safety of FdUMP[10] in treatment of HT-29 human colon cancer xenografts. Int. J. Oncol. 21:303-308 ( Year: 2002).*

Geng et al. 2011. Checkpoint Signaling, Base Excision Repair, and PARP Promote Survival of Colon Cancer Cells Treated with 5-Fluorodeoxyuridine but Not 5-Fluorouracil. PLoS One 6[12]:e28862 (Year: 2011).*

Pardee et al. 2012. Unique dual targeting of thymidylate synthase and topoisomerase1 by FdUMP[10] results in high efficacy against AML and low toxicity. Blood 119[15]:3561-3570 (Year: 2012).*

Huang et al. 2013. TDP1 repairs nuclear and mitochondrial DNA damage induced by chain-terminating anticancer and antiviral nucleoside analogs. Nuc. Ac. Res. 41[16]:7793-7803 (Year: 2013).*

Yoon (et al. 2017. Aptamer-Drug Conjugates of Active Metabolites of Nucleoside Analogs and Cytotoxic Agents Inhibit Pancreatic Tumor Cell Growth. Molec. Ther. Nucl. Ac. 6:80-88 (Year: 2017).*

Bunsdorp et al., "Mechanisms of action of FdUMP[10]: Metabolite activation and thymidylate synthase inhibition", Oncology Reports, 2007, vol. 18, pp. 287-291.

Gmeiner et al., "The applications of the novel polymeric fluoropyrimidine F10 in cancer treatment: current evidence", Future Oncol., 2016, vol. 12(17), pp. 2009-2020.

* cited by examiner

SEQUENCE LISTING

<160> NUMBER OF SEQ ID NOS: 1

<210> SEQ ID NO 1
<211> LENGTH: 11
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(10)
<223> OTHER INFORMATION: 5-fluoro-2' deoxyuridine monophosphate
<220> FEATURE:
<221> NAME/KEY: misc_feature
<222> LOCATION: (1)..(1)
<223> OTHER INFORMATION: PEG spacer appended to the 5'-terminus
<220> FEATURE:
<221> NAME/KEY: modified_base
<222> LOCATION: (11)..(11)
<223> OTHER INFORMATION: 2'-DEOXY-2'-FLUORO-beta-D-ARABINONUCLEOSIDE
    5'-TRIPHOSPHATE
<220> FEATURE:
<221> NAME/KEY: modified_base
<222> LOCATION: (11)..(11)
<223> OTHER INFORMATION: cytarabine
<220> FEATURE:
<221> NAME/KEY: misc_feature
<222> LOCATION: (11)..(11)
<223> OTHER INFORMATION: n is a, c, g, or t

<400> SEQUENCE: 1
uuuuuuuuuu n                                                    11

CYTOTOXIC FLUOROPYRIMIDINE POLYMERS AND METHODS OF USE THEREOF

RELATED APPLICATIONS AND CLAIM OF PRIORITY

This patent document is the U.S. national phase of International Patent Application No. PCT/US19/33902, filed May 24, 2019, which claims priority to U.S. Provisional Patent Application No. 62/676,511, filed May 25, 2018, the disclosure of which is fully incorporated into this document by reference.

FIELD OF THE INVENTION

This application contains a Sequence Listing which has been submitted electronically in ASCII format and is hereby incorporated by reference in its entirety. Said file, created on Dec. 4, 2024, is named SeqList2-171567-00047_ST25.txt and is 945 bytes in size.

FIELD OF THE INVENTION

The invention relates generally to the fields of medicine, oncology and molecular biology. In particular, the invention relates to cytotoxic fluoropyrimidine polymer nucleic acid molecules, compositions and methods for treating cancer in an individual.

BACKGROUND

Colorectal cancer (CRC) is one of the most common cancers in the developed world and remains a leading cause of cancer-related mortality. Five year survival rates in CRC are closely linked with stage and range from 92% for localized (stage I) disease to 53%-89% for stage II and stage III disease depending on the extent of invasion and metastatic progression. The prognosis for CRC patients with distant metastases is particularly dismal and patients with Stage IV CRC have a 5-year survival rate of <10%. Fluoropyrimidine (FP) drugs (commonly referred to as "FPs"), particularly 5-fluorouracil (5-FU), are central to the clinical management of CRC, and the use of 5-FU-based regimens provides a survival advantage for patients with stage III and high-risk stage II CRC and 5-FU-based regimens remain the cornerstone for combination regimens for metastatic disease.

FPs remain among the most effective drugs used to treat metastatic CRC (mCRC), particularly for treatment of KRAS-mutant CRC which constitutes ~40% of CRC cases and is generally non-responsive to anti-EGFR targeted agents. However, there are limitations of 5-FU that decrease its clinical efficacy. Specifically, 5-FU is rapidly degraded and excreted (~15 min half-life; 85% degraded or excreted intact) and it affects RNA function through misincorporation of the ribonucleotide form FUTP into RNA which causes gastrointestinal (GI) toxicities that are often dose-limiting and may be life-threatening. The development of a FP agent that overcomes these limitations and that would reduce the high mortality rate associated with advanced CRC is greatly needed.

SUMMARY

Described herein are novel cytotoxic fluoropyrimidine polymers, compositions, kits and methods for treating cancer (e.g., CRC) in a subject (e.g., a subject having cancer). A typical cytotoxic fluoropyrimidine polymer as described herein is a nucleic acid molecule including 5-fluoro-2'deoxyuridine monophosphate (FdUMP)[10] having a polyethylene glycol (PEG) spacer appended to the 5' terminus and a cytarabine (AraC) nucleotide appended to the 3'terminus (SEQ ID NO: 1). One example of such a nucleic acid molecule is CF10. It was discovered that CF10 displays therapeutic advantages supporting its use for the clinical management of CRC, including being well-tolerated in vivo, more rapid internalization into malignant cells than previous FPs, and an improved cytotoxicity to cancer cells relative to F10 and 5-FU. The experimental results described herein demonstrate that CF10 is highly potent to CRC cells and provides a significant survival advantage, as a result of it being highly effective at reducing progression of tumor burden, relative to both 5-FU and vehicle in an orthotopic model of CRC. The orthotopic model used replicates key aspects of human disease in terms of invasion and metastasis and CF10 was effective at reducing the occurrence of distant metastases in this model. At a molecular level, CF10 potency correlates with enhanced thymidylate synthase (TS) inhibition, consistent with efficacy resulting from increased DNA-directed effects, and likely in increased DNA topoisomerase 1 (Top1)-mediated DNA damage. As a consequence of increased DNA-directed activity, CF10 causes minimal GI-tract toxicity. Based on these experimental results, CF10 and derivatives and analogs thereof may be used for treating advanced and high-risk cancers, including CRC.

Accordingly, described herein is a nucleic acid molecule including FdUMP[10] having a PEG spacer appended to the 5'-terminus and a AraC nucleotide appended to the 3'-terminus (SEQ ID NO: 1). The nucleic acid molecule is an anti-cancer agent, is capable of being internalized by cancer cells, and is capable of inhibiting TS activity and inducing Top1-mediated DNA damage in the cancer cells (e.g., CRC cells). In an embodiment, the nucleic acid molecule has the structure:

Also described herein is a composition including a nucleic acid molecule that includes FdUMP[10] having a PEG spacer appended to the 5'-terminus and a AraC nucleotide appended to the 3'-terminus (SEQ ID NO: 1). Such a composition can further include a second anti-cancer agent (e.g., a Bromodomain-containing protein 4 (BRD4) inhibitor, a poly (ADP ribose) polymerase (PARP) inhibitor, etc.).

Further described herein is a method of treating cancer (e.g., CRC) in an individual in need thereof. The method includes administering to the individual a pharmaceutically effective amount of a nucleic acid molecule that includes FdUMP[10] having a PEG spacer appended to the 5'-terminus and a AraC nucleotide appended to the 3'-terminus (SEQ ID NO: 1), or a composition including such a nucleic acid molecule. In some embodiments, the individual is resistant to 5-FU. A nucleic acid molecule or a composition including a nucleic acid molecule can be administered at a same or different time point as administration to the individual of a second anti-cancer agent. In the method, the nucleic acid molecule is capable of being internalized by cancer cells (e.g., CRC cells) in the individual, and is capable of inhibiting TS activity and inducing Top1-mediated DNA damage in the cancer cells. In an embodiment, both a composition including a nucleic acid molecule that includes FdUMP[10] having a PEG spacer appended to the 5'-terminus and a AraC nucleotide appended to the 3'-terminus (SEQ ID NO: 1) and a second anti-cancer agent (e.g., a BRD4 inhibitor or a PARP inhibitor) are administered. Administration of a nucleic acid molecule or a composition containing the nucleic acid molecule to an individual reduces metastatic spread of the cancer cells in the individual. In some embodiments, the individual has a tumor, and administration of the nucleic acid molecule or the composition to the individual reduces tumor growth rate in the individual. The nucleic acid molecule or the composition can be administered to the individual by any suitable route, e.g., injection. In an embodiment of the method, the nucleic acid molecule has the structure:

"Colorectal Cancer" and "CRC" as used herein may be any type of CRC, including but not limited to colorectal adenocarcinoma, primary colorectal lymphomas, gastrointestinal stromal tumors, leiomyosarcomas, and melanomas that occur in the colon.

The terms "agent" and "therapeutic agent" as used herein refer to a chemical entity or biological product, or combination of chemical entities or biological products, administered to a subject to treat a disease or condition (e.g., cancer). Examples of agents include drugs and biologics.

The terms "F10" and "FdUMP[10]" are used interchangeably herein, and mean a nucleic acid molecule that is a polymeric fluoropyrimidine having 10 FdUMP nucleotides serially connected and the structure:

The terms "F10" and "FdUMP[10]" also encompass a nucleic acid molecule having 9 FdUMP nucleotides and one FdU nucleoside connected.

By the term "CF10" is meant a nucleic acid molecule including FdUMP[10] having a PEG spacer appended to the 5' terminus and a AraC nucleotide appended to the 3'terminus (SEQ ID NO: 1). CF10 is a polymeric fluoropyrimidine having the structure:

As used herein, a "CF10 derivative" or "CF10 analogue" can include a 3' terminus other than AraC, for example, any nucleotide analog that is not recognized by 3'-exonucleases (e.g., dideoxynucleotides). A CF10 derivative or CF10 analogue can include a 5' terminus other than PEG, for example, any modification that promotes cell uptake including promoting exosome-mediated uptake. A CF10 derivative or CF10 analogue may include backbone modifications such as phosphorothioate being active.

The terms "patient," "subject" and "individual" are used interchangeably herein, and mean a subject to be treated, diagnosed, and/or to obtain a biological sample from. Subjects include, but are not limited to, humans, non-human primates, horses, cows, sheep, pigs, rats, mice, dogs, and cats. A human in need of cancer treatment is an example of a subject.

As used herein, the terms "treatment" and "therapy" are defined as the application or administration of a therapeutic agent or therapeutic agents to a patient, or application or administration of the therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

Although nucleic acids, compositions, kits, and methods similar or equivalent to those described herein can be used in the practice or testing of the present invention, suitable nucleic acids, compositions, kits, and methods are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

FIGS. 2A and 2B are graphs showing that capped F10 is highly cytotoxic to HCT-116 cells and is a highly potent inhibitor of TS. 2A, Dose-response curves for CF10, F10, and 5-FU in HCT-116 cells (96 h) using a CellTiter-Glo assay (Promega, Wisconsin). Trends are similar to the NCI60 data (Table 1) and demonstrate CF10 is effective towards CRC cells that are relatively resistant to 5-FU. 2B-Graphs of TS enzymatic activity at 24 h (solid) and 48 h (checkered) for 8 nM CF10 and 100 nM 5-FU. 5-FU treatment results in short-term TS inhibition but this rebounds by 48 h to nearly levels. In contrast CF10 treatment while somewhat slower results in more complete TS inhibition at 48 h.

DETAILED DESCRIPTION

Novel cytotoxic fluoropyrimidine polymers and compositions containing them, as well as methods of using them, are described herein. A novel therapy has been developed for cancer, including e.g., CRC, based on the delivery of a nucleic acid molecule including FdUMP[10] having a PEG spacer appended to the 5' terminus and a AraC nucleotide appended to the 3'terminus (SEQ ID NO: 1) (e.g., CF10). CF10 overcomes some of the limitations of 5-FU that decrease its clinical efficacy. For example, CF10 is first converted to FdUMP, the nucleotide metabolite that specifically inhibits the folate-dependent enzyme TS, and then to the triphosphate metabolite FdUTP, which is subsequently incorporated into DNA and causes Top1-mediated DNA damage. This dual targeting of TS and Top1 specifically targets cells that have sustained proliferative signaling, a hallmark of cancer, by targeting processes critical for cell survival. CF10 was designed to reduce extracellular cleavage by nucleases in plasma and to improve cell uptake, increasing its effectiveness for treatment of solid tumors, including CRC. AraC is not efficiently removed by 3'exonucleases that are present in plasma which limits CF10 extracellular degradation thus promoting uptake of intact CF10 by endocytosis into cancer cells. AraC may be removed following cell uptake by tyrosyl DNA phosphodiesterase (Tdp1) or by nucleases present in cancer cells. In addition to protecting CF10 from extracellular degradation, AraC may contribute to the anti-cancer activity of CF10 by conversion to AraCTP following release and interfering in DNA elongation. The presence of the PEG spacer at the 5' terminus of CF10 preserves the hydrophilicity of the molecule while reducing its charge density, which may promote cell uptake and improve tumor penetration. Also, PEG may facilitate exosome incorporation which could promote cell uptake.

The experimental results described in more detail in the Examples demonstrate the therapeutic utility of CF10 that was shown to be highly potent to CRC cells. Evaluation of CF10 in the NCI60 cell line screen showed that human CRC cell lines, including HCT-116 which is a model of KRAS-mutant CRC, were responsive to CF10 at nM concentrations. Further testing confirmed the sensitivity of HCT-116 cells to CF10 and the substantial potency advantage for CF10 relative to 5-FU. To determine if the potency advantage for CF10 in cellular models of CRC translates into improved anti-cancer activity in vivo, CF10 and 5-FU were tested relative to vehicle control in both flank and orthotopic models of CRC. CF10 treatment resulted in a significant survival advantage relative to 5-FU and vehicle. The significant survival advantage of CF10 in an orthotopic model of KRAS-mutant, metastatic CRC demonstrates its potential to more effectively treat advanced and high-risk CRC than current FP options. Further, CF10 was effective at decreasing tumor growth and was very well tolerated. These studies support use of CF10 to improve outcomes in advanced cancers such as CRC.

Nucleic Acid Molecules and Compositions for Treating Cancer

In a typical embodiment, a nucleic acid molecule for treating cancer includes FdUMP[10] (ten FdUMP nucleotides serially connected) having a PEG spacer (or other modification that promotes cell uptake including promoting exosome-mediated uptake) appended to the 5'-terminus and a AraC nucleotide (or any moiety that is not recognized by 3'-exonucleases) appended to the 3'-terminus. In some embodiments, cleavage of the terminal moiety appended to the 3'-terminus occurs substantially in cancer cells.

In some exemplary embodiments, the moiety appended to the 3'-terminus is 3'-deoxy-adenine, 3'-deoxy-cytosine, 3'-deoxy-guanine, 3'-deoxy-thymine, or any analog or derivative thereof. In some embodiments, the moiety is an anti-nucleoside analog with anti-viral activity. Non-limiting examples include carbovir, acyclovir, 3TC (Lamivudine), AZT (Zidovudine), (−)-FTC, ddI (Didanosine), ddC (zalcitabine), abacavir (ABCTm), tenofovir (PMPATm), DD4FCTM (Reverset), (Stavudine), Racivir, L-FddCTM, L-FD4C, NVP (Nevirapine), DLVTM (Delavirdine), EFVTM (Efavirenz), SQVMTm (Saquinavir mesylate), RTVTm (Rifonavir), IDVTM (Indinavir), SQVTM (Saquinavir), NFVTM (Nelfinavir), APVTM (Amprenavir), and LPVTM (Lopinavir). In some embodiments, the moiety is an L-nucleoside. Non-limiting examples include 2'-deoxy-L-nucleosides, beta-L-2'-deoxythymidine, L-2'-deoxyuridines. L-FMAU (2'-fluoro-5-methyl-β-L-arabinofuranosyluridine), L-FIAU (2'-fluoro-5-iodo-β-L-arabinofuranosyluridine), L-FC (2'-fluoro-β-L-arabinofuranosylcytosine), L-FIAC (2'-fluoro-5-iodo-β-L-arabinofuranosylcytosine), L-2-C1-2'-F-2'-deoxyadenine, L-FEAU (2'-fluoro-5-ethyl-β-L-iarabinofuranosyluridine), L-arathymidine, L-fludarabine, L-araguanosine, and L-arainosine. In some embodiments, the moiety is cytarabine (AraC).

Such a nucleic acid molecule (e.g, CF10) is an anti-cancer agent, and can be used to treat any of a plurality of cancers. The nucleic acid molecules described herein are capable of being internalized by cancer cells, of inhibiting TS activity, and of inducing Top1-mediated DNA damage in the cancer cells. In one embodiment, the PEG spacer has 2, 3, 4, 5, 6, 7, 8, 9, 10, or more repeating units of $CH_2CH_2O$. In one embodiment, the cancer cells are CRC cells, and in CRC cells, CF10 was shown to be highly cytotoxic and capable of reducing tumor burden and cancer cell metastasis while causing minimal GI tract toxicity. In one embodiment, the PEG spacer has a terminal free hydroxyl. In one embodiment, the terminal hydroxyl group of the PEG spacer is derived into a group such as an ester, an amide, a carbamate, a sulfonate, a sulfonamide, a ether, a thioether, or an alkyl. The group can be optionally substituted with halide, alkyl, aryl, heteroaryl or other suitable functional group to modify the activity and bioavailability of the molecule.

Compositions for treating cancer in an individual described herein include a therapeutically effective amount of a nucleic acid molecule that includes FdUMP[10] having a PEG spacer appended to the 5'-terminus and a AraC nucleotide appended to the 3'-terminus (SEQ ID NO: 1) (e.g., CF10). Such a composition may be in a form suitable for administration either by itself or alternatively, using a delivery vehicle (e.g., liposomes, micelles, nanospheres, etc.). In some embodiments, the composition further includes a second anti-cancer agent. Examples of additional (second) anti-cancer agents that may be included in the compositions include agents that modulate the DNA damage response. Examples of such agents include poly (ADP ribose) polymerase (PARP) inhibitors and Bromodomain-containing protein 4 (BRD4) inhibitors. PARP inhibitors are known in the art, and include, for example, Olaparib, Niraparib, Talazoparib, Veliparib, Iniparib, and Rucaparib. BRD4 inhibitors are also known in the art and include, as examples, BMS-986158, TG 1601, I-BET-761, and JQ1. Another example of an anti-cancer agent that may be included in the compositions is an agent that blocks one or more immune checkpoints (e.g., a "checkpoint inhibitor") may be included in the compositions. Checkpoint inhibitors are known in the art, and include, for example, Pembrolizumab, nivolumab, durvalumab, atezolixumab, avelumab, etc.

In conjunction with the nucleic acid molecules and compositions as described herein, many other known anti-cancer agents (e.g., anti-neoplastic agents, anti-tumor agents, anti-angiogenic agents) can be used. A list of such other anti-cancer agents is included in U.S. patent application Ser. No. 15/316,160 (publication no. US 2017/0151240) which is incorporated herein by reference in its entirety.

Typically, the nucleic acid molecules and compositions are delivered to appropriate target cells in the individual (e.g., human patient or subject). A target cell is any proliferating malignant or pre-malignant cell. In one embodiment, target cells are CRC cells. CRC cells include, for example, KRAS-mutant CRC cells. In the experiments described below, CF10 showed high cytotoxicity toward proliferating malignant cells with low toxicity to normal cells.

The nucleic acid molecules and compositions described herein may be used to treat any type of cancer, including cancerous solid tumors such as sarcomas, carcinomas, and lymphomas. Specific examples of cancers include bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumors, primary or secondary brain tumors, Hodgkin's disease, chronic or acute leukemias, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non-Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblastoma, or a combination thereof.

Nucleic acid molecules and compositions containing nucleic acid molecules as described herein may be in a form suitable for administration (e.g., injection) by themselves or alternatively, using a suitable delivery vehicle. Any suitable delivery vehicles and techniques for delivering nucleic acid molecules to cells can be used. Examples of suitable delivery vehicles include liposomes, micelles, and nanospheres. In an embodiment, a delivery vehicle includes exosomes, e.g., autologous exosomes from CRC patients. Useful lipid compounds and compositions for transfer of nucleic acids are described, e.g., in PCT Publications No. WO 95/18863 and WO96/17823, and in U.S. Pat. No. 5,459,127.

Methods of Treating Cancer in an Individual in Need Thereof

Methods of treating cancer in an individual in need thereof include administering to the individual a pharmaceutically effective amount of a nucleic acid molecule as described herein, or a composition including the nucleic acid molecule, for treating (e.g., alleviating, ameliorating, curing) cancer in the individual and a pharmaceutically acceptable carrier. The methods include administration of any of the nucleic acid molecules and compositions described herein. In the methods, the nucleic acid molecule is capable of being internalized by cancer cells in the individual. In a typical embodiment, administration of a nucleic acid molecule or composition as described herein inhibits TS activity and induces Top1-mediated DNA damage in the cancer cells without affecting normal cell viability in the individual (i.e., viability of the individual's normal (non-cancerous) cells), and reduces tumor growth rate in the individual. In some embodiments, administration of the nucleic acid molecule or composition to the individual reduces metastatic spread of the cancer cells in the individual. In an embodiment, the individual in need of treatment has CRC (e.g., mCRC, stage I CRC, stage II CRC, stage III CRC, stage IV CRC). In such an embodiment, the individual may be resistant to 5-fluorouracil (5-FU).

Nucleic acid molecules for treating cancer (e.g., CF10 or derivative or analog thereof) and compositions containing the nucleic acid molecules can be administered as a monotherapy or as part of a combination therapy with any other anti-cancer agent in a method of treating cancer in an individual in need thereof. Some of the compositions described above are compositions that contain both a nucleic acid molecule for treating cancer as described herein and a second anti-cancer agent. In other embodiments of a combination therapy, a first composition may include a nucleic acid for treating cancer as described herein, and a second composition may include the second anti-cancer agent. In such embodiments, the first composition may be administered at the same time point or approximately the same time point as the second composition. Alternatively, the first and second compositions may be administered at different time points. A nucleic acid molecule for treating cancer as described herein (e.g., CF10 or derivative or analog thereof) can be used in a combination therapy that includes one or more of immunotherapy, chemotherapy, radiotherapy, and surgery. In an embodiment in which the individual being treated is also receiving immunotherapy, the immunotherapy can include, for example, a checkpoint inhibitor. In some embodiments, the individual being treated is also receiving an agent that modulates the DNA damage response (e.g., a PARP inhibitor, a BRD4 inhibitor, etc.). In some embodiments, the individual being treated with a nucleic acid molecule or composition as described herein is also receiving radiation therapy (optionally with surgery). Methods of administering radiation therapy which uses high-energy radiation (e.g., one or both of X-rays and gamma rays can be used) to shrink tumors and kill cancer cells are well known. The radiation may be delivered by a machine outside the body (external-beam radiation therapy), or it may come from radioactive material placed in the body near cancer cells (internal radiation therapy, also called brachytherapy) or alternatively, they can be used in combination. The methods described herein also include using systemic radiation therapy, which uses radioactive substances, such as radioactive iodine, that travel in the blood to kill cancer cells. (e.g., combining radioactive iododeoxyuridine with CF10 to promote tumor-specific radiation damage).

Any suitable methods of administering a nucleic acid molecule or composition as described herein to an individual may be used. In these methods, the nucleic acid molecules and compositions can be administered to an individual by any suitable route, e.g., oral, buccal (e.g., sub-lingual), parenteral (e.g., subcutaneous, intramuscular, intradermal, or intravenous), topical (i.e., both skin and mucosal surfaces, including airway surfaces), rectal, vaginal, and transdermal administration. In an embodiment, a nucleic acid molecule or composition may be administered systemically by intravenous injection. In another embodiment, a nucleic acid molecule or composition may be administered directly to a target site, by, for example, surgical delivery to an internal or external target site, or by catheter to a site accessible by a blood vessel. If administered via intravenous injection, the nucleic acid molecule or composition may be administered in a single bolus, multiple injections, or by continuous infusion (e.g., intravenously, by peritoneal dialysis, pump infusion). For parenteral administration, the nucleic acid molecule or composition is preferably formulated in a sterilized pyrogen-free form.

As indicated above, a nucleic acid molecule or composition as described herein may be in a form suitable for sterile injection. To prepare such a composition, the suitable active therapeutic agent(s) (e.g., a therapeutically effective amount of CF10) is dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution (D5W, 0.9% sterile saline). The aqueous formulation may also contain one or more preservatives (e.g., methyl, ethyl or n-propyl p-hydroxybenzoate). In cases where the therapeutic agent(s) is only sparingly or slightly soluble in water, a dissolution enhancing or solubilizing agent can be added, or the solvent may include 10-60% w/w of propylene glycol or the like. The nucleic acid molecules and compositions described herein may be administered to an individual (e.g., rodents, humans, nonhuman primates, canines, felines, ovines, bovines) in any suitable formulation according to conventional pharmaceutical practice (see, e.g., *Remington: The Science and Practice of Pharmacy* (21st ed.), ed. A. R. Gennaro, Lippincott Williams & Wilkins, (2005) and *Encyclopedia of Pharmaceutical Technology*, (3$^{rd}$ ed.) eds. J. Swarbrick and J. C. Boylan, Marcel Dekker, CRC Press, New York (2006), a standard text in this field, and in USP/NF). A description of exemplary pharmaceutically acceptable carriers and diluents, as well as pharmaceutical formulations, can be found in Remington: supra. Other substances may be added to the nucleic acid molecules and compositions to stabilize and/or preserve them.

The therapeutic methods described herein in general include administration of a therapeutically effective amount of the nucleic acid molecules and compositions described herein to an individual (e.g., human) in need thereof, particularly a human. Such treatment will be suitably administered to individuals, particularly humans, suffering from, having, susceptible to, or at risk for a disease, disorder, or symptom thereof (e.g., cancer). Determination of those individuals "at risk" can be made by any objective or subjective determination by a diagnostic test or opinion of a subject or health care provider. Numerous prognostic markers or factors for categorizing CRC patients or individuals for likely outcome of treatment are known. See, e.g., Lin PS & Semrad T J, *Molecular Testing for the Treatment of Advanced Colorectal Cancer: An Overview* Methods Mol Biol. 2018 1765:281-297; and Zacharakis et al., *Predictors of survival in stage IV metastatic colorectal cancer* Anticancer Res, 2010 30 (2): 653-660. In some embodiments, the individual in need of treatment is afflicted with a relapsed CRC (e.g., the individual was previously treated for CRC, then in partial or complete remission for CRC, and then the CRC has returned).

Effective Doses

The nucleic acid molecules and compositions described herein are preferably administered to an individual in need thereof (e.g., human having cancer) in an effective amount, that is, an amount capable of producing a desirable result in a treated individual. Desirable results include one or more of, for example, inhibiting TS activity and inducing Top1-mediated DNA damage in the cancer cells, reducing tumor size, reducing cancer cell metastasis, and prolonging survival. Such a therapeutically effective amount can be determined according to standard methods. Toxicity and therapeutic efficacy of the nucleic acid molecules and compositions utilized in the methods described herein can be determined by standard pharmaceutical procedures. As is well known in the medical and veterinary arts, dosage for any one individual depends on many factors, including the individual's size, body surface area, age, the particular composition to be administered, time and route of administration, general health, and other drugs being administered concurrently. A delivery dose of a composition as described herein is determined based on preclinical efficacy and safety. In the experiments described below, CF10 was administered at a dose of 300 mg/kg i.p. twice per week. In an embodiment, an effective amount includes administration once every 5, 6, or 7 days.

Kits

Described herein are kits for treating cancer (e.g., CRC) in a subject. A typical kit includes a composition including a pharmaceutically acceptable carrier (e.g., a physiological buffer) and a therapeutically effective amount of a nucleic acid molecule including FdUMP[10] having a PEG spacer appended to the 5' terminus and a AraC nucleotide appended to the 3' terminus (SEQ ID NO: 1) (e.g., CF10); and instructions for use. A kit can also include a second anti-cancer agent. Kits also typically include a container and packaging. Instructional materials for preparation and use of the compositions described herein are generally included. While the instructional materials typically include written or printed materials, they are not limited to such. Any medium capable of storing such instructions and communicating them to an end user is encompassed by the kits herein. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The present invention is further illustrated by the following specific examples. The examples are provided for illustration only and should not be construed as limiting the scope of the invention in any way.

Example 1—the Fluoropyrimidine Polymer CF10 Displays Potent Anti-Tumor Activity in an Orthotopic Model of CRC A 2nd generation FP polymer, CF10, was tested to determine if polymeric delivery of DNA-directed metabolites enhances potency toward CRC cell lines and improves efficacy even while reducing systemic toxicities relative to 5-FU. The 2nd generation FP polymer CF10 was tested for potency in CRC cell lines including HCT-116, a model of KRAS-mutant CRC. Antitumor activity of CF10 was tested in a flank tumor model. CF10 efficacy was evaluated in an orthotopic CRC model with tumor growth, survival, and decreased metastases as endpoints. CF10 displayed enhanced potency to human CRC cells and effectively inhibited TS. CF10 was well tolerated in vivo and displayed antitumor activity in HCT-116 xenograft tumors with systemic administration. CF10 treatment resulted in a markedly improved survival advantage relative to both 5-FU and vehicle control in an HCT-116-luc orthotopic model (median survival 55 days vs 31 and 33 days, respectively). 5-FU treatment causes serious GI toxicities including decreased villus length while crypts and villi from CF10-treated mice were indistinguishable from control. HCT-116-luc orthotopic tumors metastasize to liver, lung and other organs and decreased metastases occurred in CF10-treated mice. CF10 displayed improved efficacy, reduced GI toxicity, and reduced metastatic spread relative to 5-FU in an orthotopic CRC model.

Materials & Methods

Cell Lines and Drugs. HCT-116 human CRC cells were supplied by GRCF Biorepository & Cell Center (Johns Hopkins University). HCT116 cells were infected with UBC-GFPLuc-LV by the Cell and Viral Vector Laboratory at Wake Forest School of Medicine to generate luciferase-expressing HCT116-luc cells. These cells also express GFP. All human CRC cell lines were maintained in Dulbecco's Modified Eagle Medium (DMEM; Lonza, Switzerland) supplemented with 10% fetal bovine serum (FBS; Sigma, St. Louis, Missouri). Cell lines were cultured in conditions of 37° C. and 5% $CO_2$ and were confirmed negative for *mycoplasma*. CF10 (ST Pharm Co., South Korea) and 5-fluorouracil (Sigma, St. Louis, Missouri) were used for drug treatment. CF10 was dissolved in phosphate buffered saline (PBS) while 5-FU was prepared at 50 mg/mL in DMSO and diluted with PBS or DMEM. For in vivo studies, CF10 was prepared in sterile PBS and a maximum of 200 μL was injected i.p. 5-FU was initially dissolved in 1 M $NH_4OH$, diluted with sterile PBS, and balanced with 1 M HCl to neutral pH. All drugs were filtered using a 0.22 μm filter before injection.

Cell Culture. Cells were seeded in 96-well plates at the appropriate density in 200 μL medium and incubated for 37° C. overnight for cell attachment. Drug concentrations were determined using a UV-Vis spectrophotometer using the $A_{260}$ molar extinction coefficient values of 0.027 μg/mL$^-$ $_1$cm$^{-1}$ for CF10 and 7.07 mM$^{-1}$cm$^{-1}$ for 5-FU. Compounds were serially-diluted in either water or DMSO (final DMSO percentage<1%) to a stock concentration, and an equal amount of drug was added to the exponentially growing cells for each tested concentration. All drugs were filtered in 0.22 μm filter before use.

Cell Viability. CellTiter-Glo (Promega, Wisconsin) was used to determine cell viability. Assays were performed according to the manufacturer's instructions. Cell viability was normalized and calculated as a relative percentage of the averaged vehicle control.

Thymidylate Synthase Activity. TS activity assays were performed using well-established procedures. HCT116 cells were plated at a density of $1.0$-$1.5 \times 10^6$ cells in 100 mm$^2$ plates. Cells were grown overnight in DMEM media with 10% FBS to allow the cells to adhere and begin to grow. Drugs were then added to the medium and the cells were incubated for the indicated time (24 h or 48 h). Cells were then harvested in 25 mM Tris-HCl, pH 7.4 with Complete Protease Inhibitor Cocktail present (as per instructed, Roche), put through two freeze/thaw cycles, and vigorously vortexed. The lysates were centrifuged at 10,000×g for 10 min at 4° C. The supernatants were assayed for protein concentration and TS catalytic activity. TS catalytic assays were performed in a final volume of 200 μL containing freshly prepared 75 μM 5,10 methylene tetrahydrofolate in 0.5 M NaOH (Schircks Laboratories, Switzerland), 10 μM dUMP, 200,000 dpm of 3H-dUMP (Moravek Biochemicals), 100 μM 2-mercaptoethanol, and 25 mM $KH_2PO_4$, pH 7.4. Cell lysate aliquots (400 μg of protein) were added to the reaction buffer and lysis buffer was used to adjust the final volume. The reaction mixture was incubated at 37° C. for 30 min, then stopped by addition of 100 μL of ice-cold, 20% TCA. Stopped reactions were maintained 5 min on ice. Two hundred μL of activated charcoal solution (10 g activated charcoal, 0.25 g BSA, 0.25 g dextran sulfate, in 100 mL of water) was then added, and the mixture was vortexed briefly and maintained at RT for 10 min. Reactions were then centrifuged, and aliquots of the supernatant were read by scintillation counting.

Animal Model. Balb/c athymic nude mice and Balb/c immunocompetent mice (Charles River) were housed and subjected to experiments in accordance with the protocols approved by the Institutional Animal Care and Use Committee (IACUC) at Wake Forest School of Medicine. All of the animal experiments were performed on six-to-eight-week-old female BALB/c mice.

Xenograft Model. HCT116 cells ($3 \times 10^6$ cells) were suspended in ice-cold PBS and mixed 1:1 with Matrigel and subcutaneously injected into the flanks of Balb/nude mice. Tumor growth and mice health were monitored daily until the tumor reached a volume of 100-200 mm$^3$ (about two weeks). Tumor measurements were taken using electronic digital calipers twice a week, along with mouse weight. Tumor volume (V) was calculated as $V=\pi/6$ (L×W$^2$). 5-FU (70 mg/kg 2×/wk every other week) or CF10 (300 mg/kg) were dosed by intraperitoneal (i.p.) injection using a 28-gauge needle. Mice requiring removal from study due to large tumor burden or weight-loss were euthanized in accord with AVMA guidelines.

Orthotopic Colorectal Model. Protocol was followed per Tseng et al.'s previous study (Tseng W. et al., Vis Exp, 2007 (10): p. 484). A xenograft tumor was formed as described above using HCT116-luc cells. Once the tumor reached a size large enough for transplantation, mice were euthanized and tumor tissue was removed. The tumor was divided into 2-3 mm pieces and placed in PBS on ice. BALB/c mice were put under anesthesia, and the abdomen was prepped with a betadine solution. A laparotomy was performed in the abdomen and the cecum was exposed. The cecal wall was slightly damaged to allow cell invasion. A piece of tumor tissue was then attached to the outside of the cecum by a figure-8 stitch using a 9-O-nylon suture. The cecum is returned to the cavity and the abdomen wall is closed up using 6-0 coated vycryl sutures. A rectal thermometer monitored the internal temperature of the mice during surgery. Mouse recovery was monitored closely and mice were given Meloxicam every day for 3 days to alleviate pain along with normal saline to keep the mice hydrated. Tumor volume and cell progression was monitored using an IVIS live imaging system for evaluated total proton flux. Two independent studies were performed with identical procedures except in the second study 5-FU (n=9) was dosed 1×/wk at 30 mg/kg rather than 1×/wk at 100 mg/kg, which was toxic. Subsequent evaluation of 5-FU dosed at 70 mg/kg also showed GI toxicity (see below). CF10 was dosed 2×/week every week at 360 mg/kg (n=8 study 1; n=2 in study 2). All drugs, or vehicle (0.9% saline; n=8 study 1; n=6 study 2) were administered by i.p. injection in 200 µL volume.

Animal Imaging. Pierce D-Luciferin (Thermo Scientific) was injected subcutaneous using a 28-gauge needle 15 minutes before imaging. Mice were placed in an anesthesia chamber with 1.5% isoflurane and then transferred to the IVIS stage under 2% isoflurane using a nose cone placing the mice on their back. IVIS Lumina LT Series III machine was used for all mouse images. All images were analyzed at the end of the time experiment using the same Living Image software. A region of interest was placed on the mouse' midsection and determined the total flux in that region. The region of interest remained identical for each mouse. Graphs were plotted as total flux per mouse for each week.

GI Tract Toxicity. BALB/c immunocompetent mice were put into two cohorts with three groups within each cohort (n=2). 5-FU (70 mg/kg), CF10 (200 mg/kg), and PBS were injected i.p. once every three days for a total of four injections for one cohort and a single injection for the other cohort. Tissue collection was performed 24 h after the last injection. Mice were euthanized using $CO_2$ and cervical dislocation and the small intestine was removed quickly. The intestine was washed in PBS and coiled onto a cassette before fixing with 4% paraformaldehyde at 4° C. for 24 h, then in 70% ethanol at 4° C. until it was paraffin embedded and cut into 4 µm slices before staining with H&E. Embedding and staining was all done by the Comparative Pathology Laboratory at Wake Forest School of Medicine.

Statistical Analysis. All statistical analyses were conducted using SAS 9.4 using a mixed models approach. Baseline flux from IVIS imaging measurement, group, time and group-by-time interaction were included as fixed effects. The animals were included as random effects to account for the within animal correlation. Survival differences among treatment groups were determined using a log-rank test.

Histology Analysis. Tissues from select mice from all treatment groups were removed from animals after undergoing euthanasia by intra-cardiac administration of KCl solution. In some instances, mice were injected with luciferin ~20 min prior to euthanasia and tissue extraction to permit IVIS imaging of extracted tissue. Tumors were weighed after removal and in instances where there was suspicion of possible metastases to liver, lung, or other organs tissue from these organs was removed and if luciferin was administered prior to euthanasia, these tissues were imaged using the IVIS system. All tissues were fixed in 10% neutral buffered formalin for 24 h followed by transfer to 70% ethanol. Following routine processing in xylene, tissues were sectioned at 4 µm and stained with Hematoxylin and Eosin and evaluated by light microscopy by a veterinary pathologist.

Results

Figure 1:
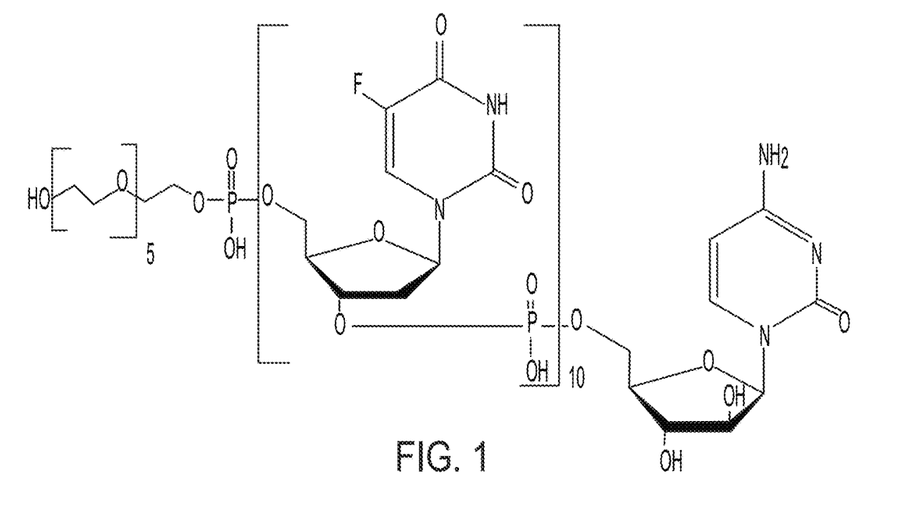
FIG. 1 is the structure of CF10 in one embodiment (SEQ ID NO: 1).

CF10 is Highly Potent to CRC Cells. Evaluation of the $2^{nd}$ generation FP polymer CF10 (FIG. 1) in the NCI60 cell line screen revealed CF10 was more potent than F10 to CRC cell lines tested and that both FP polymers were considerably more potent than 5-FU to all CRC cell lines for which data were available. The results are summarized in Table 1. The lowest CF10 dose tested (10 nM) exceeded the GI50 value for three CRC cell lines: HCT-116, HT-29, and COLO205. Importantly, even the least sensitive CRC cell line included in the NCI60 (SW620) was still sensitive to C10 at low micromolar concentrations ($GI_{50}=2.57\times10^{-6}$ M).

TABLE 1

Compilation of GI50 values for CF10, F10, and 5-FU from the NCI 60 cell line screen

|  | CF10 | F10 | 5-FU | Fold (CF10/5-FU) |
| --- | --- | --- | --- | --- |
| COLO205 | $<1.00 \times 10^{-8}$ | $1.29 \times 10^{-7}$ | $6.92 \times 10^{-6}$ | >692 |
| HCT-116 | $<1.00 \times 10^{-8}$ | $1.10 \times 10^{-8}$ | $4.07 \times 10^{-6}$ | >407 |
| HT-29 | $<1.00 \times 10^{-8}$ | $4.79 \times 10^{-7}$ | $6.76 \times 10^{-6}$ | >676 |
| HCT-15 | $1.78 \times 10^{-7}$ | $3.09 \times 10^{-7}$ | $5.62 \times 10^{-6}$ | 32 |
| SW620 | $2.57 \times 10^{-6}$ | $5.01 \times 10^{-5}$ | $2.82 \times 10^{-5}$ | 11 |
| HCC2998 | ND | $2.34 \times 10^{-8}$ | $1.51 \times 10^{-6}$ | ND |
| KM-12 | ND | $3.55 \times 10^{-6}$ | $8.71 \times 10^{-6}$ | ND |

ND-not determined

Figure 2A:
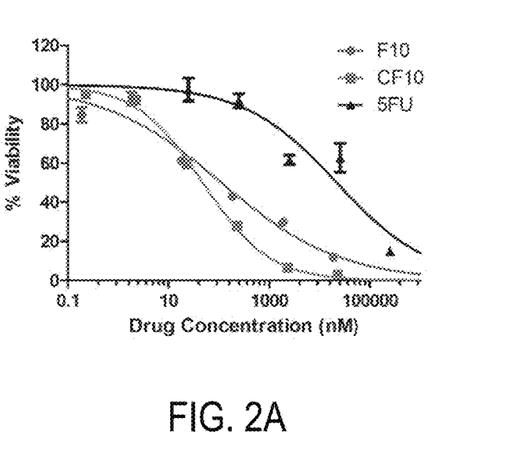

HCT-116 cells were selected for further analysis as this is a human CRC cell line that is considered 5-FU resistant due to its MSI-H status and is also KRAS mutant. Time-dependent cytotoxicity studies showed CF10 is somewhat slower to work than F10 as evidenced by being slightly less cytotoxic at shorter timepoints but ultimately is more effective than F10 at decreasing cell viability (FIG. 2A). Overall, CF10 is 2.35-fold more potent than F10 (48 nM vs 113 nM) and 452-fold more potent than 5-FU (48 nM vs 21 µM) to HCT-116 cells. These differences are of similar magnitude to the potency differences determined from the NCI60 $GI_{50}$ values.

Figure 2B:
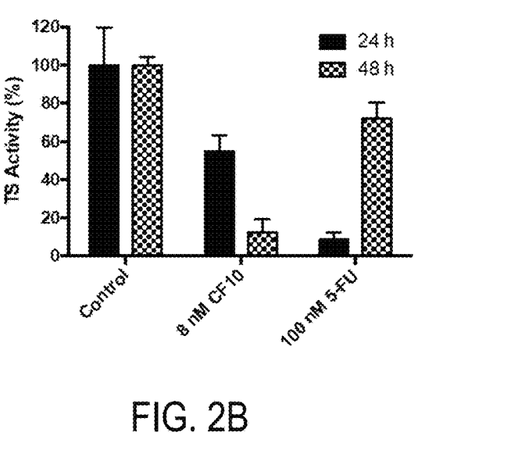

Since TS is an established target of FP drugs, whether CF10 treatment decreased TS enzymatic activity in HCT-116 cells was assessed. Cells treated with 8 nM CF10 (~$IC_{70}$ dose) resulted in almost complete abrogation of TS activity at 48 h (FIG. 2B). In contrast, cells treated with 100 nM 5-FU display reduced TS activity at 24 h that has rebounded to ~75% control values by 48 h. Hence CF10 treatment effectively inhibits TS at much lower doses that 5-FU and inhibition of TS enzymatic activity is sustained longer.

HCT-116 in vivo Xenograft Study. Based on the strong potency advantage for CF10 relative to 5-FU in in vitro studies, CF10 efficacy in HCT-116 xenografts was evaluated to determine if the potency advantage observed in vitro translates into a significant efficacy advantage in vivo.

First evaluated was the efficacy of CF10 relative to 5-FU in a flank xenograft model to determine if i.p. injection of CF10 resulted in a systemic anti-tumor effect. Several doses and schedules have been used to evaluate 5-FU efficacy in similar flank tumor models using human CRC tumor cells in immunocompromised mice and in this initial tumor model 5-FU at 70 mg/kg i.p. 2× per week every other week was evaluated. CF10 was dosed at 300 mg/kg i.p. 2×/week the same dose used in previous in vivo studies with F10 that established potent anti-tumor activity and minimal systemic toxicity.

Figure 3A:
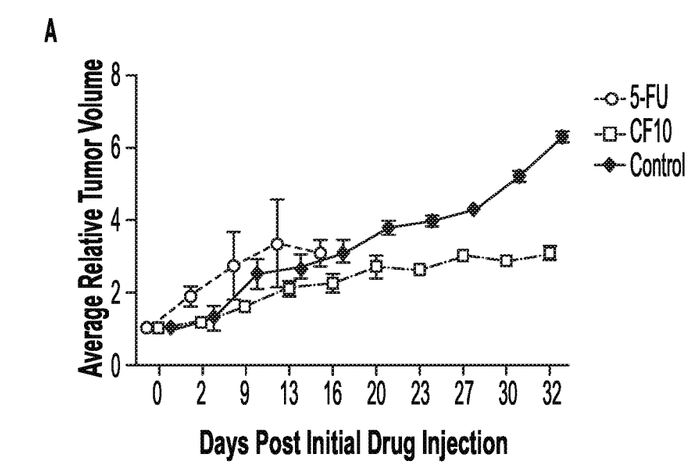
FIGS. 3A, 3B, 3C, 3D and 3E are a pair of graphs and a series of micrographs showing that CF10 is efficacious in a flank tumor model following i.p. administration and causes no significant GI-tract toxicity at efficacious doses. 3A, Graph of tumor growth rates (mean+/−SEM) for HCT-116 flank tumors in mice treated with 5-FU (blue), CF10 (red), or saline (black). All drugs were administered by i.p. injection. 3B, Average lengths of crypts and villi in GI-tracts of mice treated with saline (white), 5-FU (hatched), or CF10 (cross-hatched). Average villus length in 5-FU-treated mice is decreased while CF10 treatment has no effect. C-E, microscopy showing a segment of GI-tract from a representative mouse treated with vehicle, 3C; 5-FU, 3D; or CF10, 3E.
Figure 3B:
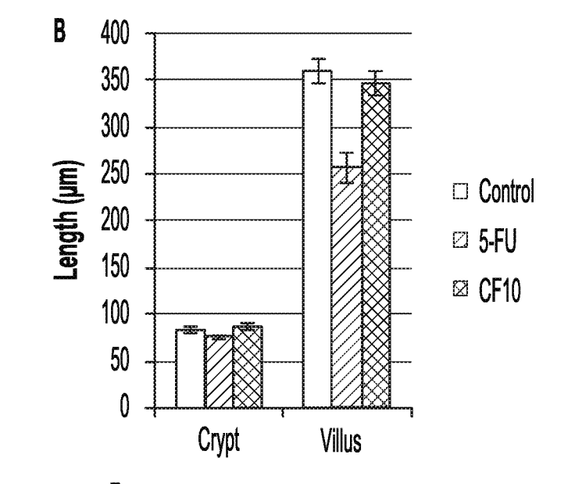
Figure 3C:
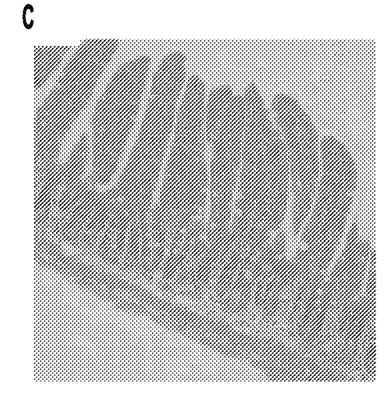
Figure 3D:
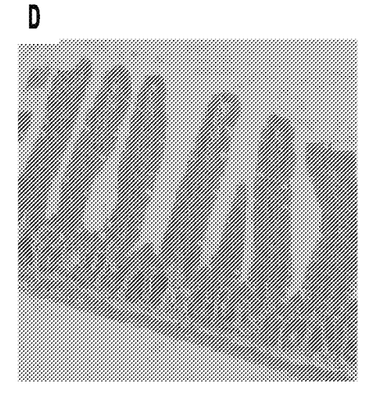
Figure 3E:
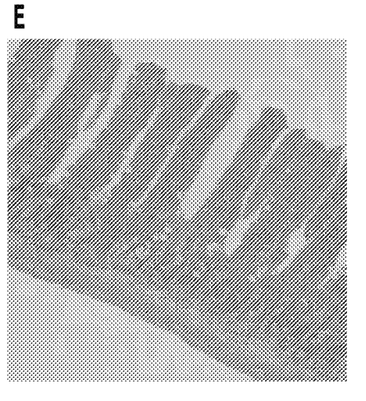
Figure 7:
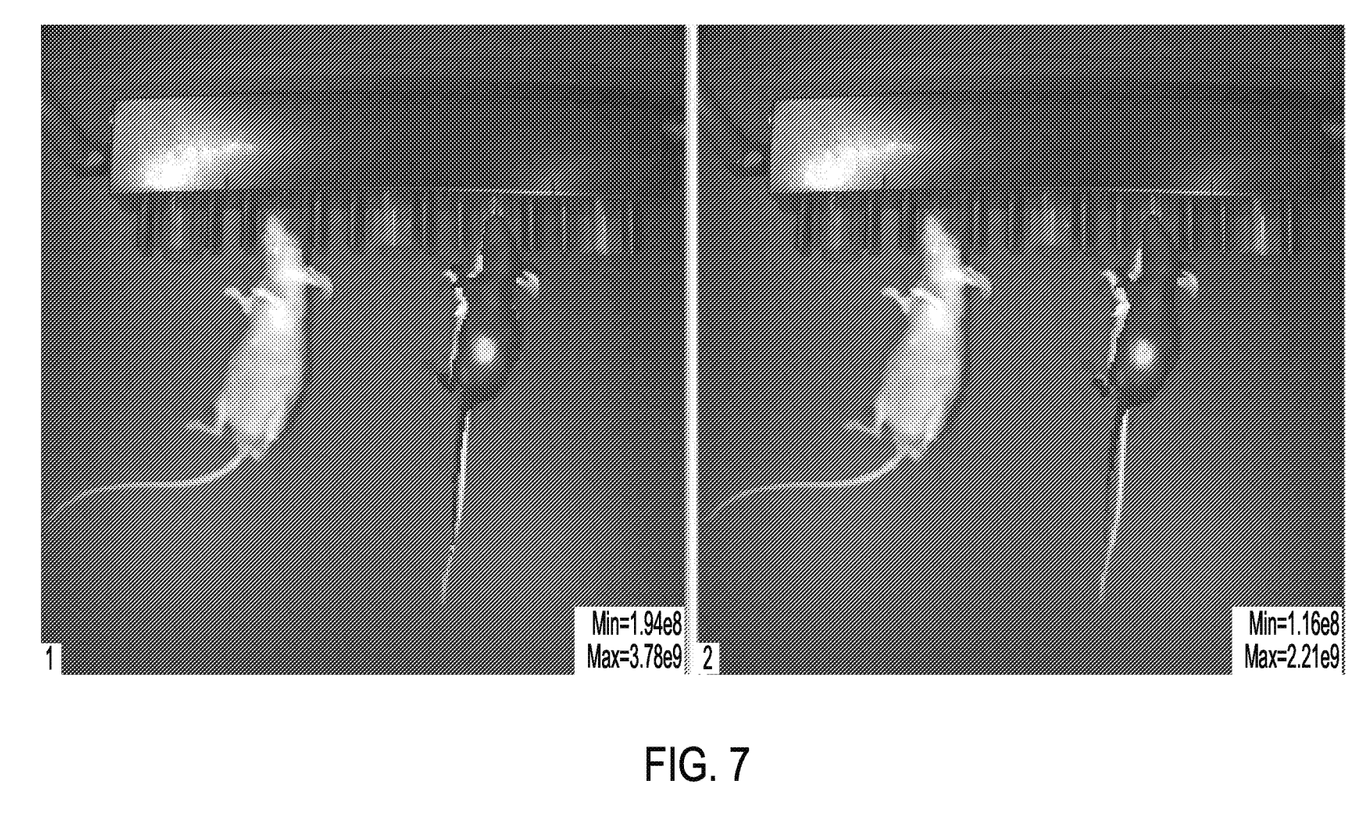
FIG. 7 is a pair of images of a control (left mouse) and a conjugate (right mouse) at 48 hours (hrs).
Figure 8:
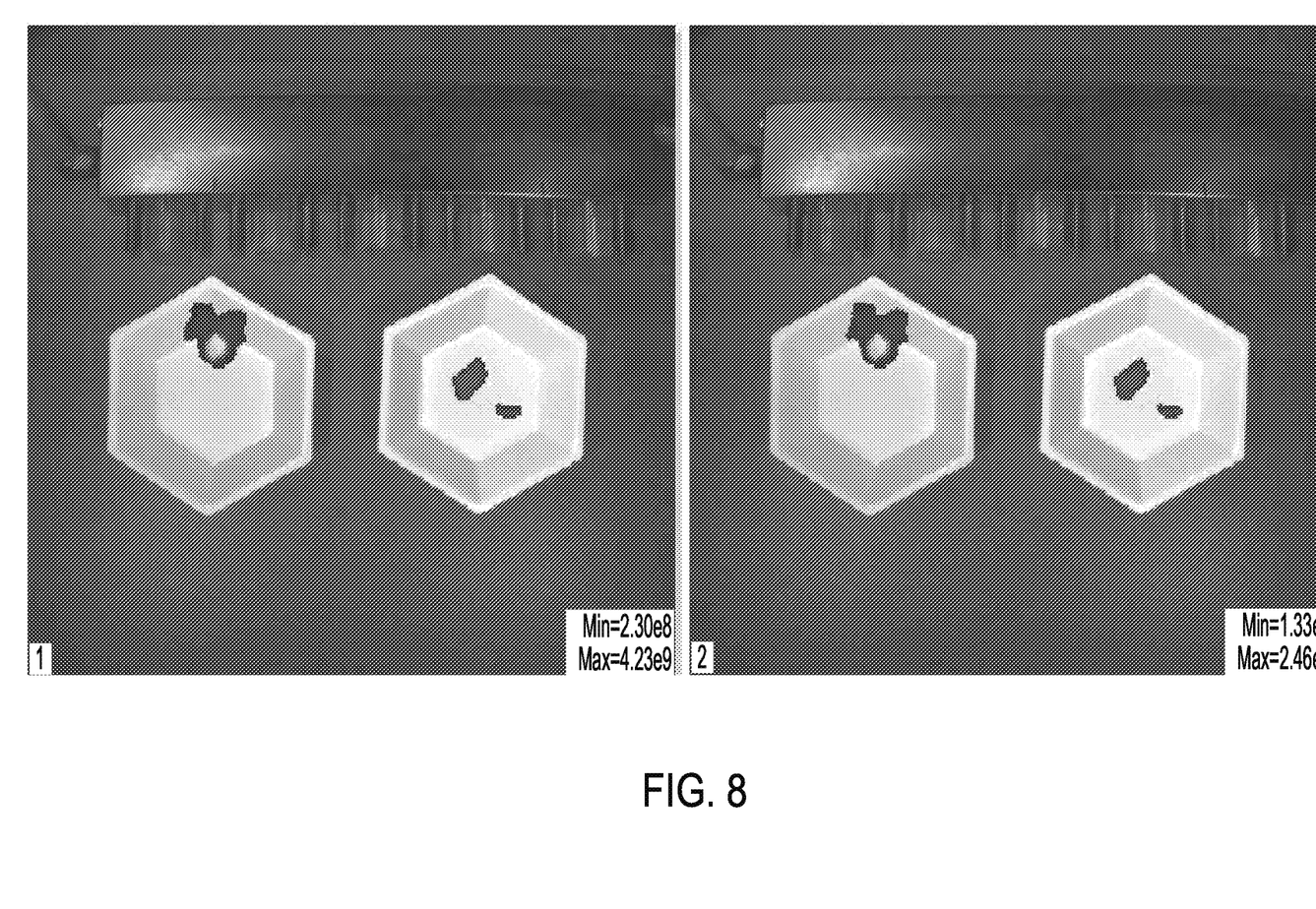
FIG. 8 is a pair of images of a tumor (left) and a liver (right) from a mouse treated with conjugate at 48 hrs showing uptake in tumor relative to liver from the same animal.

Tumor volumes rapidly increased in vehicle-treated mice requiring euthanasia of all mice 32-days post initial drug injection (FIG. 3A). Tumor growth rates for 5-FU-treated mice were similar to control, however mice treated with 5-FU displayed greater weight loss than mice in the other treatment groups and all mice required euthanasia by day 16 post-treatment. In contrast, CF10-treated mice experienced minimal weight loss and displayed decreased tumor growth rates. The results demonstrate CF10 is well-tolerated in vivo and displays strong anti-tumor activity to flank xenograft tumors with i.p. administration consistent with entry of active compound into the circulation. Subsequent evaluation of biodistribution using a fluorescent CF10 analog showed widespread tissue distribution at 48 h, including in tumor tissue, while the free dye was cleared within 48 h (FIG. 7). FIG. 8 shows uptake in tumor relative to liver from the same animal treated with conjugate at 48 hrs.

Subsequent analysis of GI-tract tissue from mice treated with a single dose of 5-FU (70 mg/kg) revealed even this lower dose significantly decreased average villus length relative to control mice while average crypt and villus lengths for mice treated with CF10 at 200 mg/kg, which delivers equivalent fluoropyrimidine as the 70 mg/kg dose of 5-FU, was not distinguishable from control (FIG. 3B-3E).

Figure 4A:
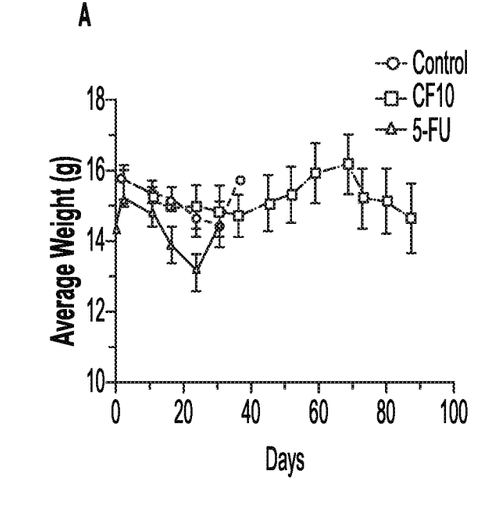
FIGS. 4A, 4B and 4C are a series of graphs showing that CF10 treatment inhibits tumor growth in an orthotopic model and provides a significant survival advantage relative to vehicle and 5-FU treatment. 4A, Graph of mouse weights for control, CF10, and 5-FU treatment groups. 4B, Graph of flux from HCT-116-luc orthotopic xenografts. Differences in the rate of change in flux among the groups were not significant during the first three weeks of treatment however the groups then diverged and flux rate was significantly lower in CF10 treated mice relative to vehicle or 5-FU treated mice. 4C, Kaplan-Meier plot showing a survival advantage for CF10 relative to vehicle and 5-FU. Differences in survival were significant based on Log-Rank test (chi-square 24.7, 2 degrees of freedom p<0.0001).

CF10 Inhibits Tumor Growth & Improves Survival. The efficacy of CF10 relative to 5-FU and vehicle-only was next evaluated in an orthotopic model of human CRC developed using HCT-116-luc cells. Tumor growth rate and survival were considered as endpoints for distinguishing effects among treatment groups. In contrast to mice treated with vehicle or 5-FU, mice treated with CF10 displayed relatively stable weights and on average gained weight during a substantial portion of the study (FIG. 4A). Mice treated with CF10 (300 mg/kg) also remained active throughout the study with no signs of drug-related toxicity.

Figure 4B:
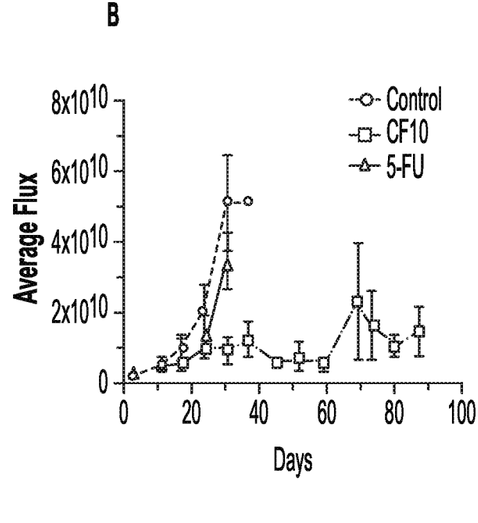
Figure 4C:
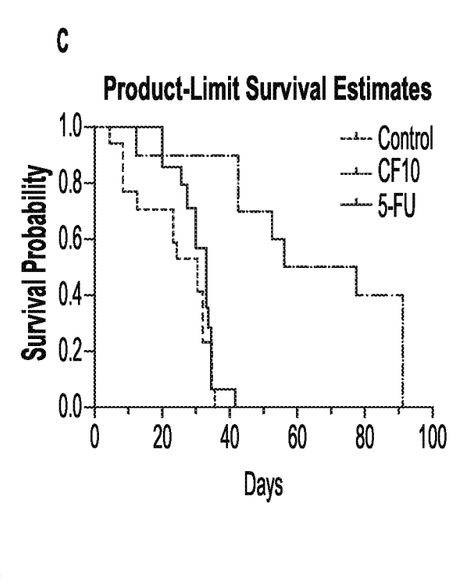
Figure 5A:
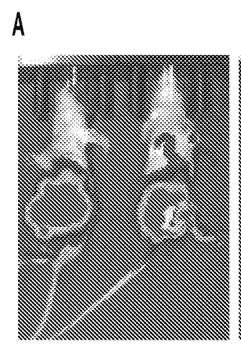
FIGS. 5A, 5B, 5C, and 5D are a series of photographs and a graph showing that CF10 treatment inhibits tumor growth. 5A-5C, representative IVIS images for mice treated with vehicle control (5A), 5-FU (5B), or CF10 (5C). All images are from mice 5 weeks post-treatment. 5D, graph showing differences in signal (average flux) from HCT-116-luc orthotopic xenografts. Data from all mice in each treatment group that were alive at week 5 post-treatment were combined and averaged. Data are consistent with improved survival upon CF10 treatment resulting from decreased tumor growth. (** p<0.01).
Figure 5B:
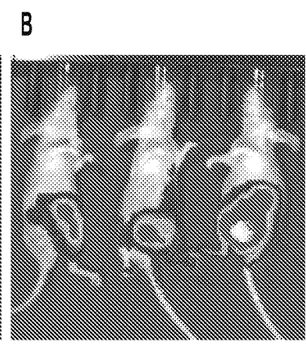
Figure 5C:
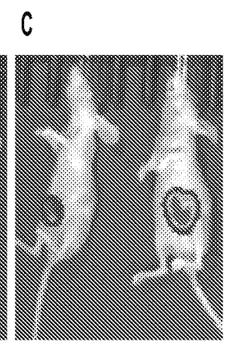
Figure 5D:
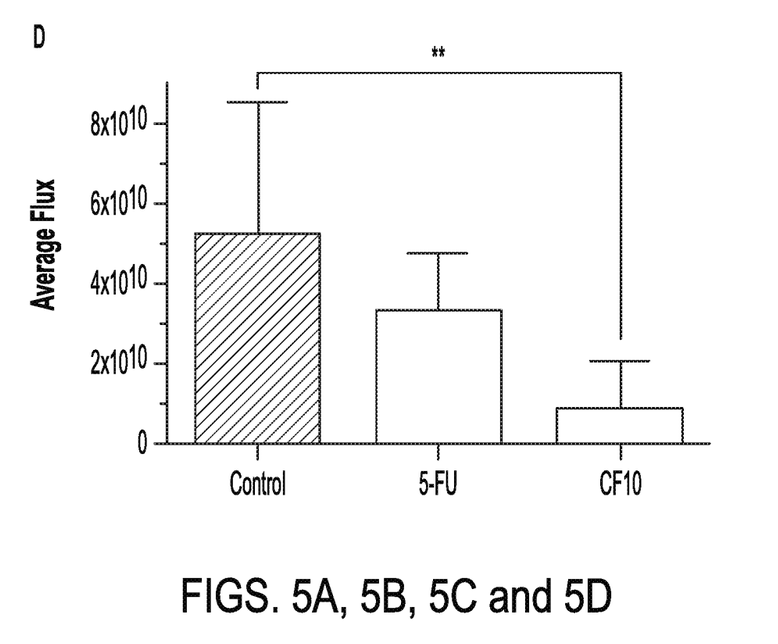

Tumor growth rate data was further analyzed to determine if improved survival with CF10 treatment was associated with inhibition of tumor growth. A summary of tumor growth rates for the three treatment groups is included in FIG. 4B and representative IVIS images from the three treatment groups and summary of the week 5 flux values is presented in FIG. 5. Changes in flux levels among 5-FU-, control-, and CF10-treated mice were analyzed using a mixed models approach. In this model, baseline flux, group, time and group-by-time interaction were included as fixed effects. The animals were included as random effects to account for the within animal correlation. The overall model showed a highly significant time-by-group interaction suggesting that the change in flux values differed among groups. The CF10 group had a slower rate of change (increase) in flux than the other two groups, with the control and 5-FU groups both showing larger increases over time. When these effects were examined during the first 3 weeks of the study, there were no significant differences in the rate of change in flux among the treatment groups. However, when the data between 3-6 weeks was examined, it was determined that the control and 5-FU groups both had a higher rate of change (i.e. increase in flux) relative to the CF10 group. The data are consistent with the enhanced survival for CF10-treated mice relative to control and 5-FU-treated mice is due to decreased tumor growth. Interestingly, while 5-FU did not improve survival relative to control, 5-FU treatment does decrease tumor growth relative to control in this model although these effects are considerably reduced relative to CF10. The data indicate CF10 is much more effective than 5-FU at inhibiting growth of HCT-116-luc orthotopic tumors and this, in concert with the reduced GI-tract toxicity of CF10 (FIG. 3B-3E) contributes to a highly significant survival advantage for CF10 treatment (FIG. 4B).

CF10 treatment also resulted in markedly prolonged survival (avg 67.4 days) relative to vehicle control (avg 30.9 days). When survival times among groups were examined, a highly significant difference was found based on the Log-Rank test (chi-square 24.7, 2 degrees of freedom p<0.0001)—with the CF10 animals having much longer survival (median 55 days) than control or 5-FU (33 days and 31 days, respectively). A Kaplan-Meier presentation of the survival data is displayed in FIG. 4B. The results demonstrate CF10 improves survival in an orthotopic model of HCT-116-luc CRC while 5-FU has no significant effect on survival in this model.

Figure 6:
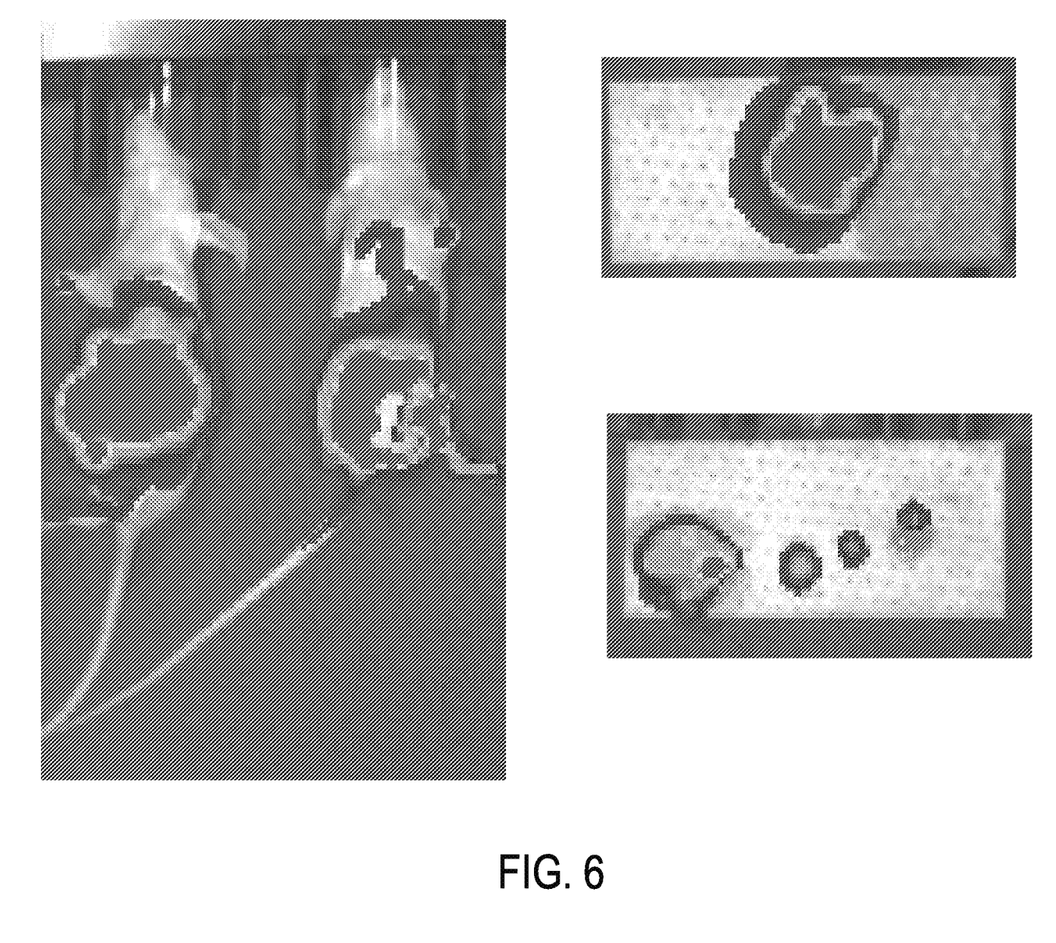
FIG. 6 is a series of representative IVIS images of control and treated mice.

Detection of Metastases. Metastatic colon cancer remains highly lethal and treatments that suppress metastatic progression would be highly valuable. Putative metastatic tissues from representative mice treated with either 5-FU or vehicle control were identified. Selected mice that were deemed to require euthanasia from morbidities associated with large tumor burden (i.e. lethargy, hunched posture) at week 5 were subject to autopsy following euthanasia. IVIS images were obtained prior to euthanasia. The primary tumors from each mouse were then removed, and liver, lung, kidney and other tissues were examined for gross morphological features consistent with metastases. Putative metastatic tissue was evident in $2/4$ of 5-FU-treated mice and in $3/5$ of the vehicle-treated group. The origin of the putative metastatic tissue as having developed from the primary tumor comprised of HCT-116-luc cells was confirmed by ex vivo IVIS imaging in all cases. Representative IVIS images are included in FIG. 6. No CF10-treated mice were euthanized at this time since they did not display morbidities related to tumor burden. Further, IVIS images demonstrated much lower tumor burden in CF10-treated mice. One otherwise viable CF10-treated mouse was euthanized at week 8 and autopsy did not indicate any metastatic tissue. Further, the primary tumor from the CF10-treated mouse was considerably smaller (0.4 g) than the average tumor burden from either 5-FU-treated mice (1.0 g) or mice treated with vehicle only (1.7 g), even though the tumor from the CF10-treated mouse was extracted three weeks later than for mice treated with either vehicle or 5-FU.

In summary, the results described above demonstrate CF10 displays therapeutic advantages supporting its use for the clinical management of CRC. CF10 is highly potent to CRC cells (Table 1; FIG. 2) and provides a significant survival advantage relative to both 5-FU and vehicle in an orthotopic model of CRC (FIG. 4A). The survival advantage for CF10 results from it being highly effective at reducing progression of tumor burden (FIG. 4B; FIG. 5). The orthotopic model used replicates key aspects of human disease in terms of invasion and metastasis (FIG. 6) and CF10 appears to be effective at reducing the occurrence of distant metastases in this model. At a molecular level, CF10 potency correlates with enhanced TS inhibition (FIG. 2C) consistent with efficacy resulting from increased DNA-directed effects. As a consequence of increased DNA-directed activity, CF10 causes minimal GI-tract toxicity (FIG. 3).

OTHER EMBODIMENTS

Any improvement may be made in part or all of the nucleic acid molecules, composition, kits, and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A nucleic acid molecule comprising FdUMP[10] having a polyethylene glycol (PEG) spacer appended to the 5'-terminus and a moiety appended to the 3'-terminus, wherein the moiety is cytosine arabinoside.

2. The nucleic acid molecule of claim 1, wherein the nucleic acid molecule is capable of being internalized by cancer cells.

3. The nucleic acid molecule of claim 2, wherein the nucleic acid molecule is capable of inhibiting thymidylate synthase (TS) activity and inducing DNA topoisomerase 1 (Top1)-mediated DNA damage in the cancer cells.

4. The nucleic acid molecule of claim 2, wherein the cancer cells are colorectal cancer (CRC) cells.

5. The nucleic acid molecule of claim 1, wherein the moiety is cytosine arabinoside (Ara-C).

6. The nucleic acid molecule of claim 1, wherein the PEG spacer has from 3 to 10 repeating units of $CH_2CH_2O$.

7. The nucleic acid molecule of claim 1, wherein the nucleic acid molecule has the structure:

8. A composition comprising the nucleic acid molecule of claim 1.

9. The composition of claim 8, further comprising a second anti-cancer agent.

10. The composition of claim 9, wherein the second anti-cancer agent is a BRD4 inhibitor or a PARP inhibitor.

11. A method of treating cancer in an individual in need thereof, comprising administering to the individual a pharmaceutically effective amount of the nucleic acid molecule of claim 1.

12. The method of claim 11, wherein the cancer is CRC.

13. The method of claim 11, wherein the individual is resistant to 5-fluorouracil (5-FU).

14. The method of claim 11, wherein the nucleic acid molecule is administered at a same or different time point as administration to the individual of a second anti-cancer agent.

15. The method of claim 11, wherein the nucleic acid molecule is capable of being internalized by cancer cells in the individual.

16. The method of claim 15, wherein the cancer cells are CRC cells.

17. The method of claim 15, wherein the nucleic acid molecule is capable of inhibiting TS activity and inducing Top1-mediated DNA damage in the cancer cells.

18. The method of claim 11, wherein the nucleic acid molecule has the structure:

19. The method of claim 11, further comprising administering a second anti-cancer agent selected from the group consisting of a BRD4 inhibitor and a PARP inhibitor.

20. The method of claim 11, wherein administration of the nucleic acid molecule of claim 1 to the individual reduces metastatic spread of the cancer cells in the individual.

21. The method of claim 11, wherein the individual has a tumor, and administration of the nucleic acid molecule of claim 1 to the individual reduces tumor growth rate in the individual.

22. The method of claim 11, wherein the nucleic acid molecule of claim 1 is administered to the individual by injection.

\* \* \* \* \*